United States Patent
Zentgraf et al.

(10) Patent No.: US 9,393,080 B2
(45) Date of Patent: *Jul. 19, 2016

(54) SURGICAL NAVIGATION FOR REPAIR OF HEART VALVE LEAFLETS

(71) Applicant: NeoChord, Inc., Eden Prairie, MN (US)

(72) Inventors: John Zentgraf, Minneapolis, MN (US); Terry Peters, London Ontario (CA)

(73) Assignee: NeoChord, Inc., Eden Prairie, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/598,821

(22) Filed: Jan. 16, 2015

(65) Prior Publication Data
US 2015/0190207 A1 Jul. 9, 2015

Related U.S. Application Data

(63) Continuation of application No. 13/692,027, filed on Dec. 3, 2012, now Pat. No. 8,938,283.

(60) Provisional application No. 61/565,795, filed on Dec. 1, 2011.

(51) Int. Cl.
*A61B 19/00* (2006.01)
*A61B 17/29* (2006.01)
(Continued)

(52) U.S. Cl.
CPC ............. *A61B 19/5244* (2013.01); *A61B 5/062* (2013.01); *A61B 8/0841* (2013.01);
(Continued)

(58) Field of Classification Search
CPC ........... A61B 17/0469; A61B 17/0482; A61B 17/29; A61B 19/50; A61B 19/5244; A61B 19/56; A61B 2017/00243; A61B 2017/00526; A61B 2017/00783; A61B 2017/06042; A61B 2019/507; A61B 2019/5251; A61B 2019/5276; A61B 2019/528; A61B 2019/5291; A61B 2560/0223; A61B 5/062; A61B 8/0841; A61B 8/12; A61B 8/4245; A61B 8/461; A61B 8/463; A61B 8/464; A61B 8/465; A61B 8/58
See application file for complete search history.

(56) References Cited

U.S. PATENT DOCUMENTS

| | | | | |
|---|---|---|---|---|
| 8,241,274 | B2 * | 8/2012 | Keogh | ................... A61F 2/2433 606/27 |
| 8,428,690 | B2 * | 4/2013 | Li | ............................ A61B 5/06 382/128 |

(Continued)

FOREIGN PATENT DOCUMENTS

| WO | WO 2011/070477 A1 | 6/2011 |
|---|---|---|
| WO | WO 2011/137336 A1 | 11/2011 |

OTHER PUBLICATIONS

PCT/US2012/067563, International Search Report dated Mar. 13, 2013, 3 pages.

(Continued)

*Primary Examiner* — Michael Rozanski
(74) *Attorney, Agent, or Firm* — Patterson Thuente Pedersen, P.A.

(57) ABSTRACT

To improve the overall navigation process for minimally invasive repair of heart valve leaflets, an augmented reality technique capable of providing a robust three-dimensional context for transesophogeal echocardiography data has been developed. In the context of various embodiment of the invention, augmented reality essentially refers to a system in which the primary environment is virtual but the environment is augmented by real elements. In this real-time environment, the surgeon can easily and intuitively identify the tool, surgical targets, and high risk areas, and view tool trajectories and orientations.

21 Claims, 17 Drawing Sheets

(51) Int. Cl.
*A61B 5/06* (2006.01)
*A61B 8/12* (2006.01)
*A61B 8/08* (2006.01)
*A61B 8/00* (2006.01)
*A61B 17/04* (2006.01)
*A61B 17/00* (2006.01)
*A61B 17/06* (2006.01)

(52) U.S. Cl.
CPC ............... *A61B 8/12* (2013.01); *A61B 8/4254* (2013.01); *A61B 8/461* (2013.01); *A61B 8/465* (2013.01); *A61B 8/58* (2013.01); *A61B 17/0469* (2013.01); *A61B 17/29* (2013.01); *A61B 19/50* (2013.01); *A61B 19/56* (2013.01); *A61B 8/463* (2013.01); *A61B 8/464* (2013.01); *A61B 17/0482* (2013.01); *A61B 2017/00243* (2013.01); *A61B 2017/00526* (2013.01); *A61B 2017/00783* (2013.01); *A61B 2017/06042* (2013.01); *A61B 2019/507* (2013.01); *A61B 2019/528* (2013.01); *A61B 2019/5251* (2013.01); *A61B 2019/5276* (2013.01); *A61B 2019/5291* (2013.01); *A61B 2560/0223* (2013.01)

(56) References Cited

U.S. PATENT DOCUMENTS

| | | | |
|---|---|---|---|
| 8,465,500 B2 | 6/2013 | Speziali | |
| 8,532,352 B2* | 9/2013 | Ionasec | G06T 7/0032 382/128 |
| 8,938,283 B2* | 1/2015 | Zentgraf | A61B 8/461 382/131 |
| 2006/0229594 A1 | 10/2006 | Francischelli et al. | |
| 2008/0188873 A1* | 8/2008 | Speziali | A61B 17/0469 606/144 |
| 2009/0105729 A1 | 4/2009 | Zentgraf | |
| 2009/0105751 A1 | 4/2009 | Zentgraf | |
| 2010/0030061 A1 | 2/2010 | Canfield et al. | |
| 2010/0174297 A1 | 7/2010 | Speziali | |
| 2012/0184971 A1 | 7/2012 | Zentgraf et al. | |
| 2013/0035757 A1 | 2/2013 | Zentgraf et al. | |
| 2013/0150710 A1 | 6/2013 | Zentgraf et al. | |
| 2014/0039324 A1 | 2/2014 | Speziali | |

OTHER PUBLICATIONS

PCT/US2012/067563, International Preliminary Examination Report, dated Jun. 3, 2014, 5 pages.

* cited by examiner

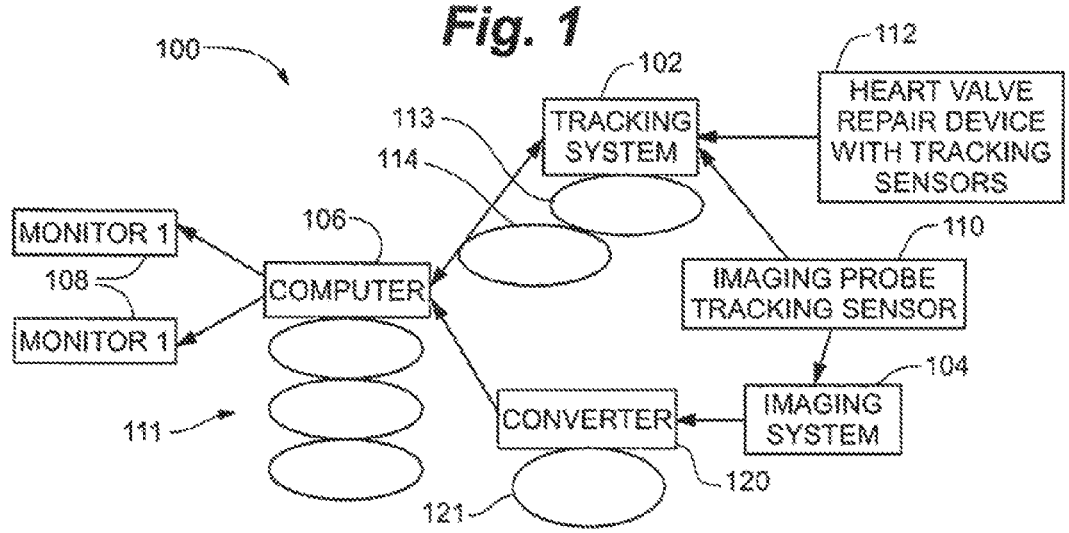
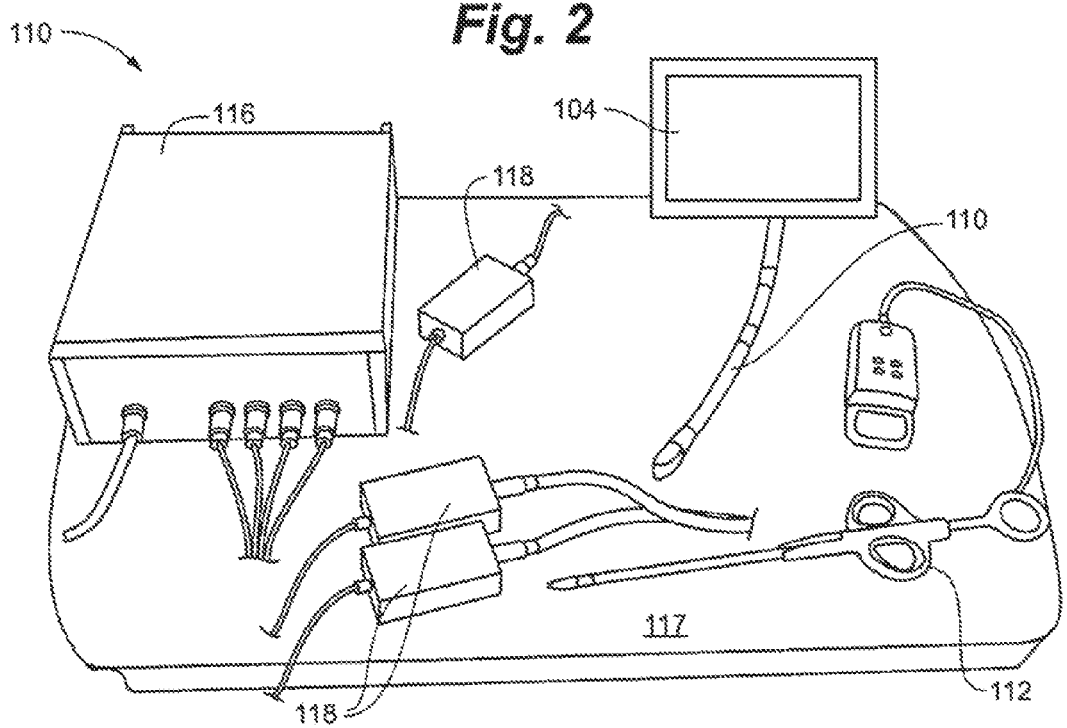

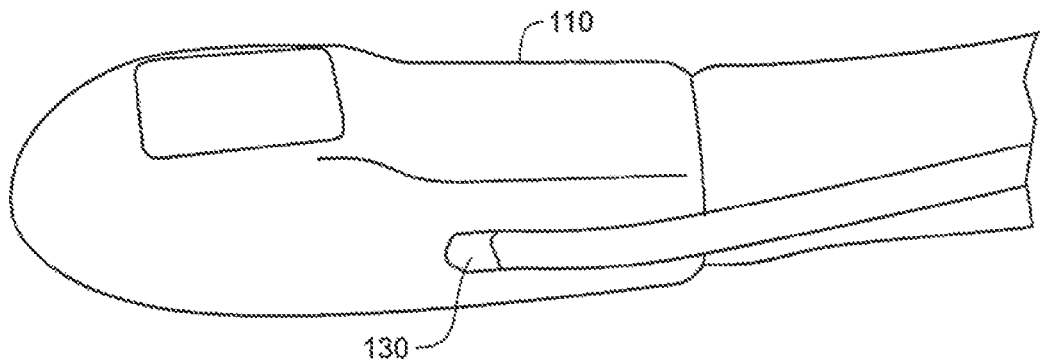
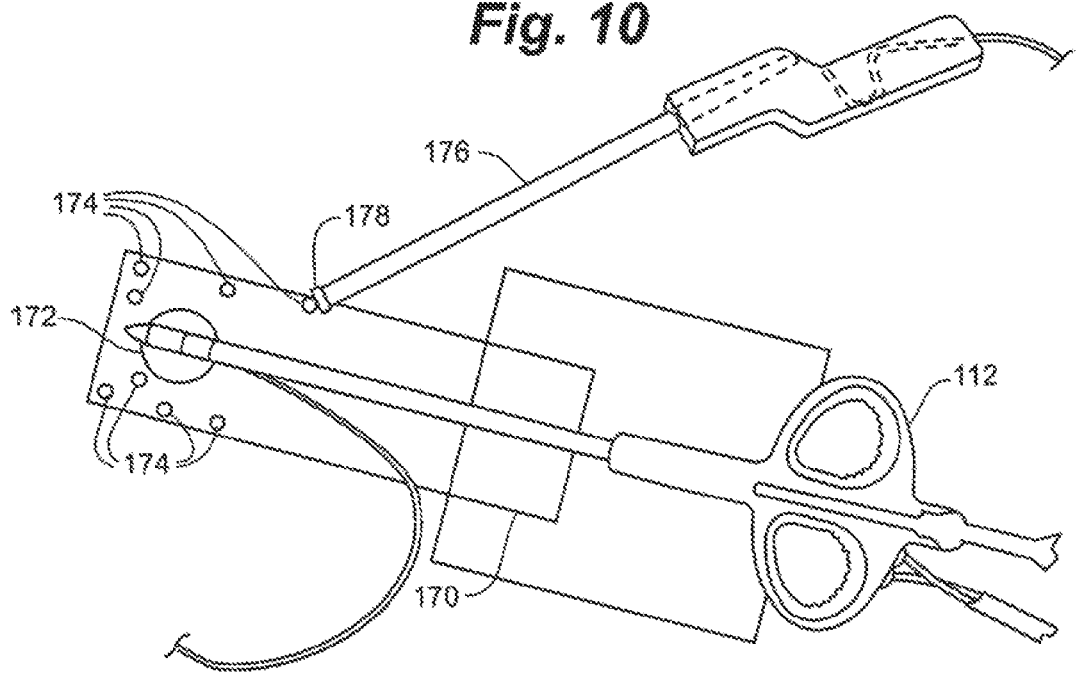

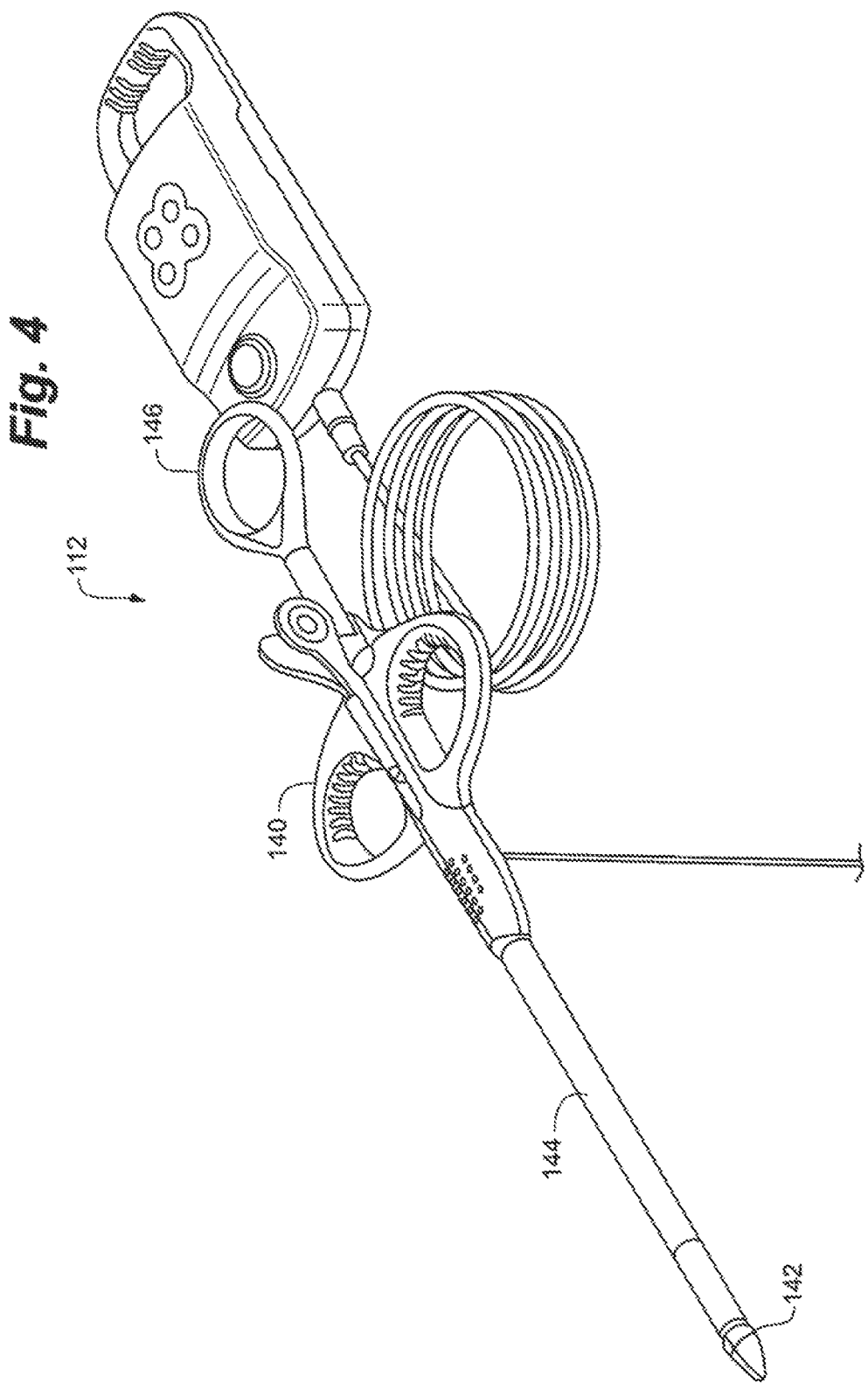

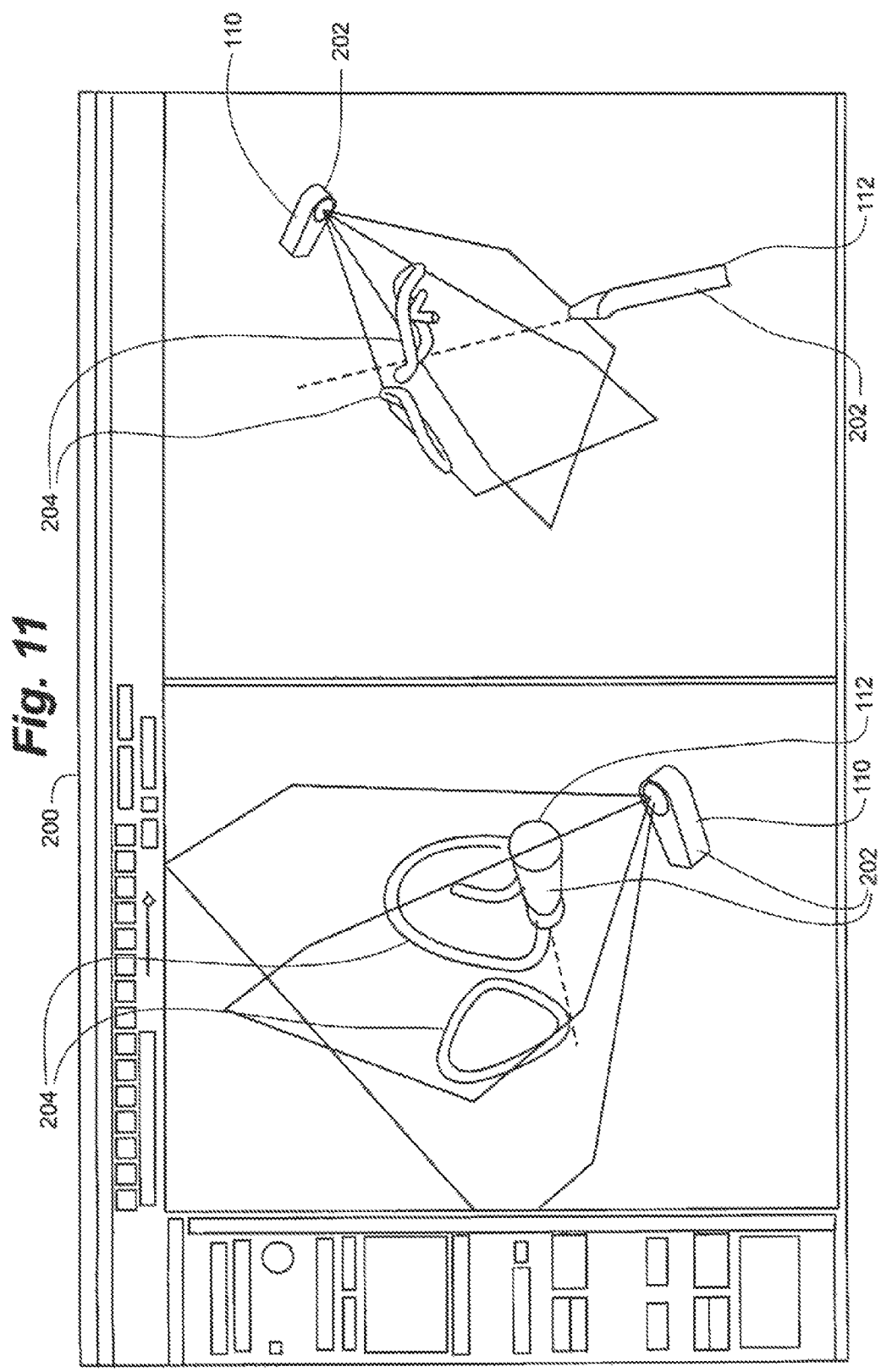

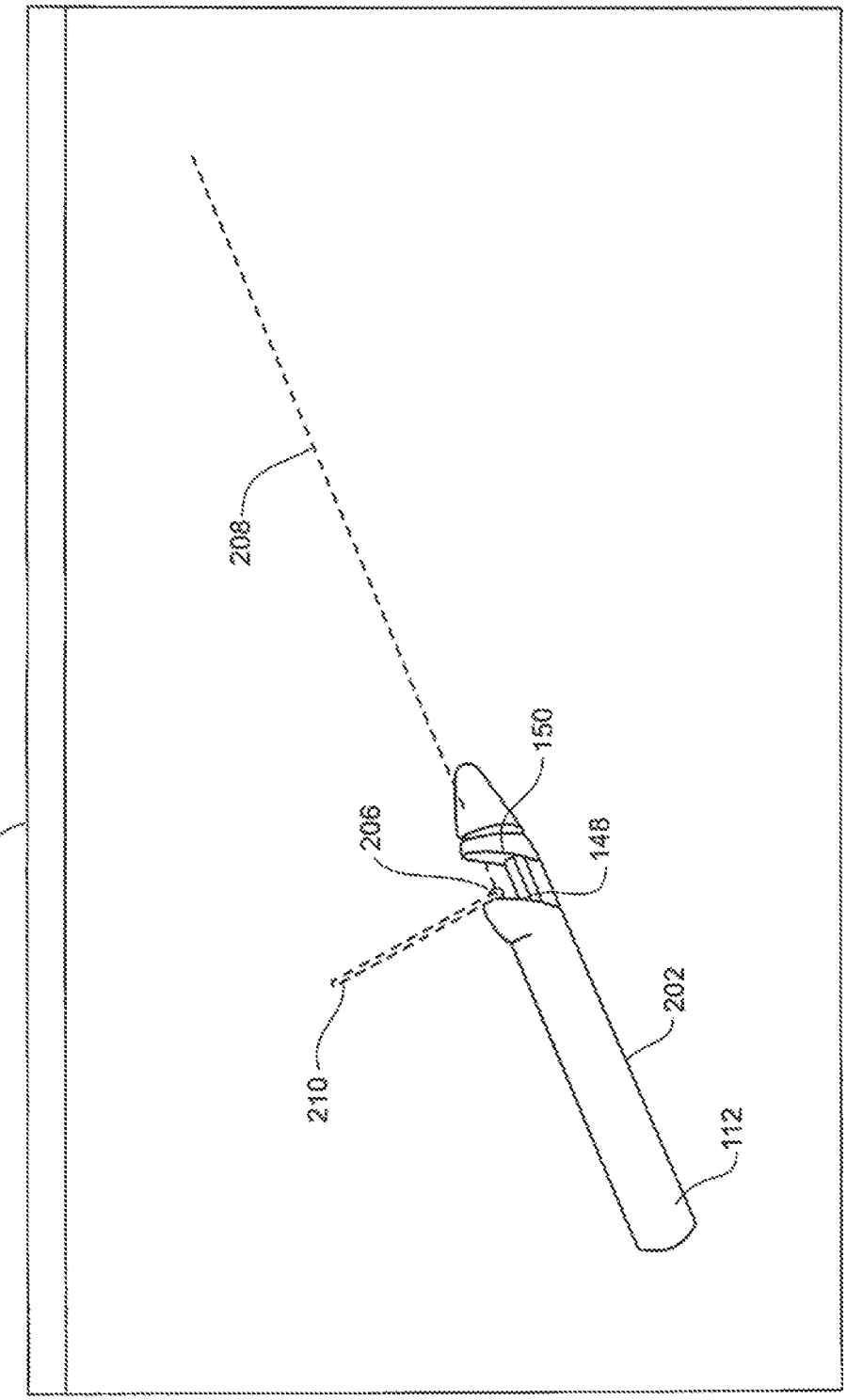

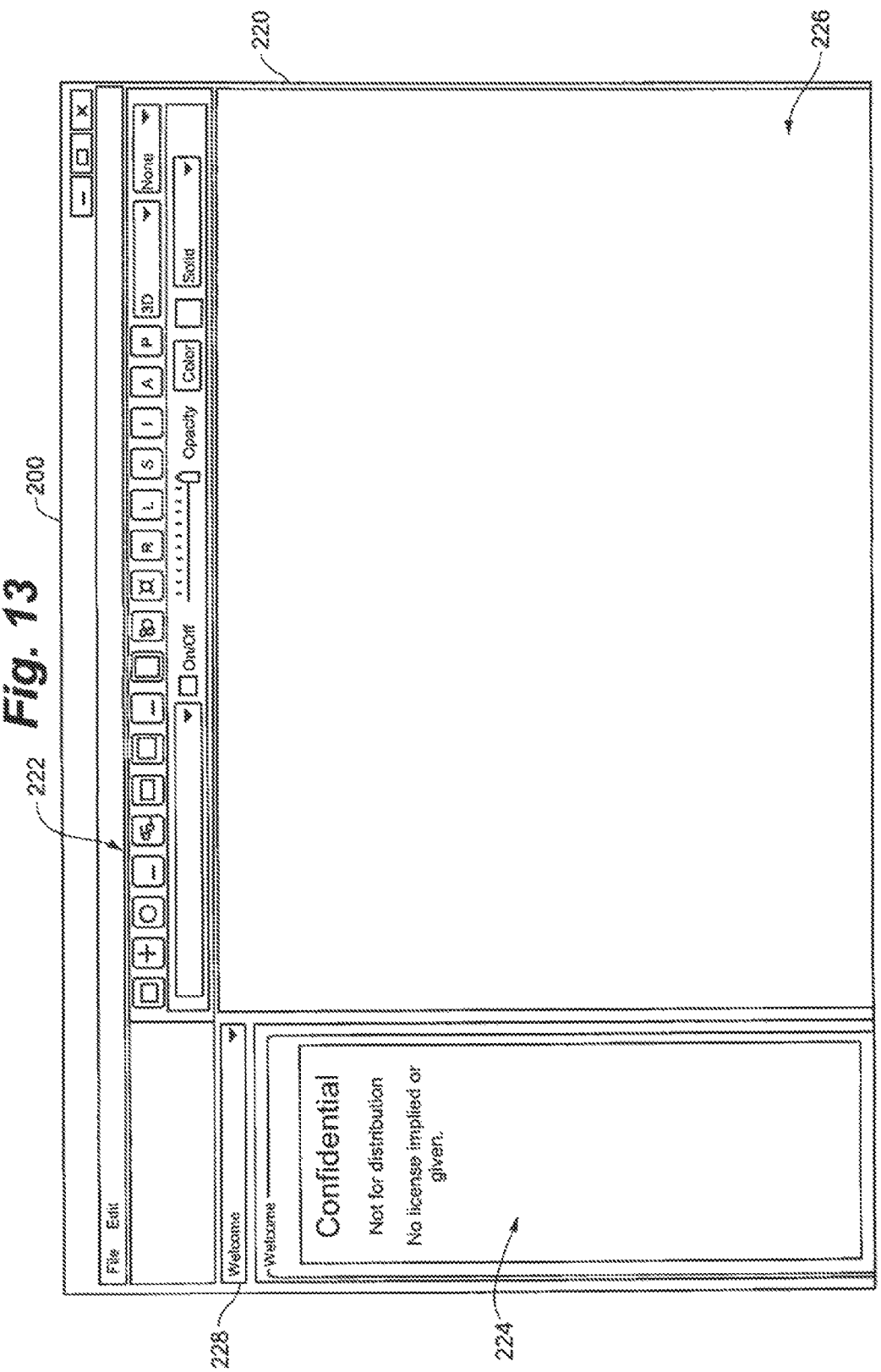

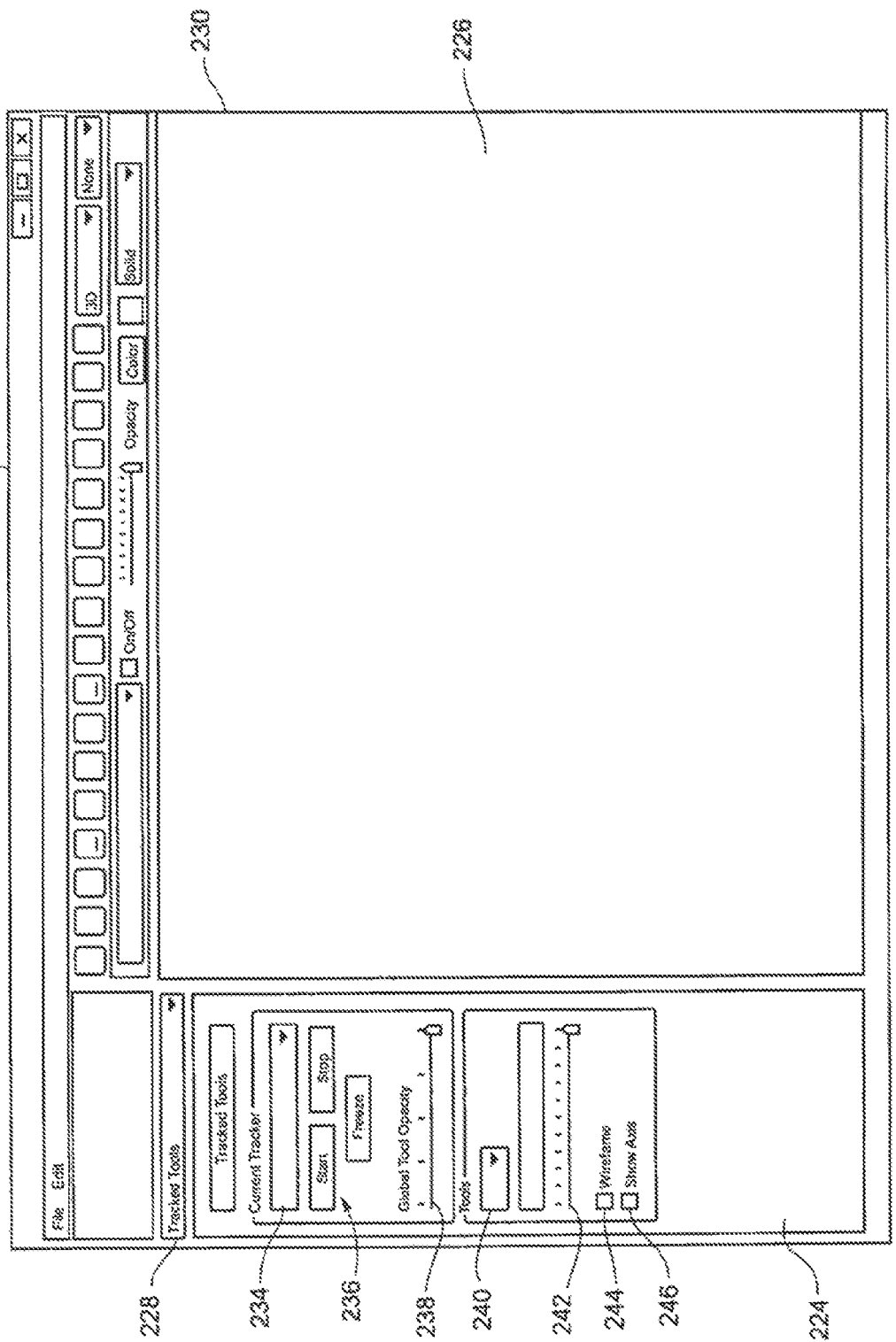

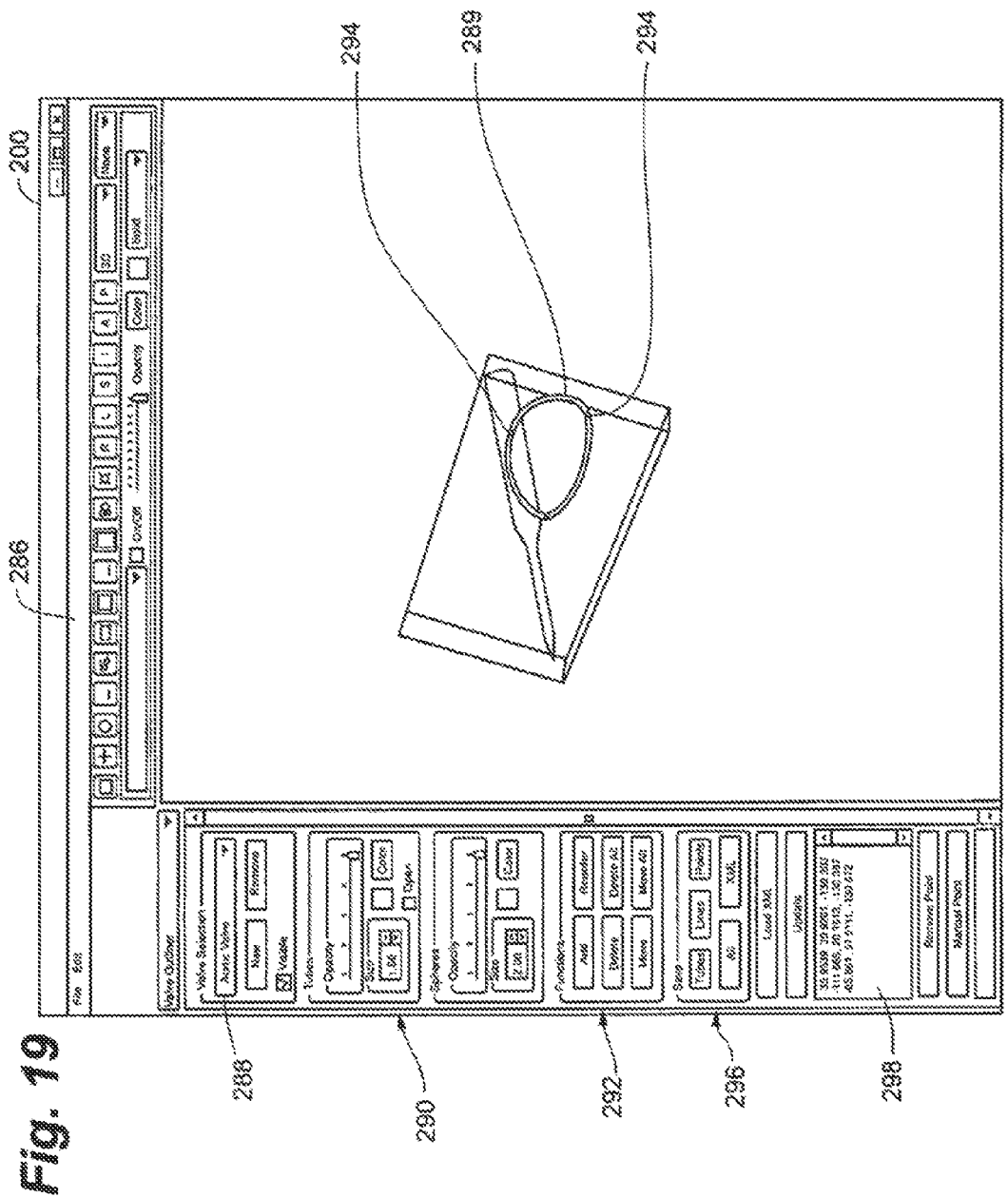

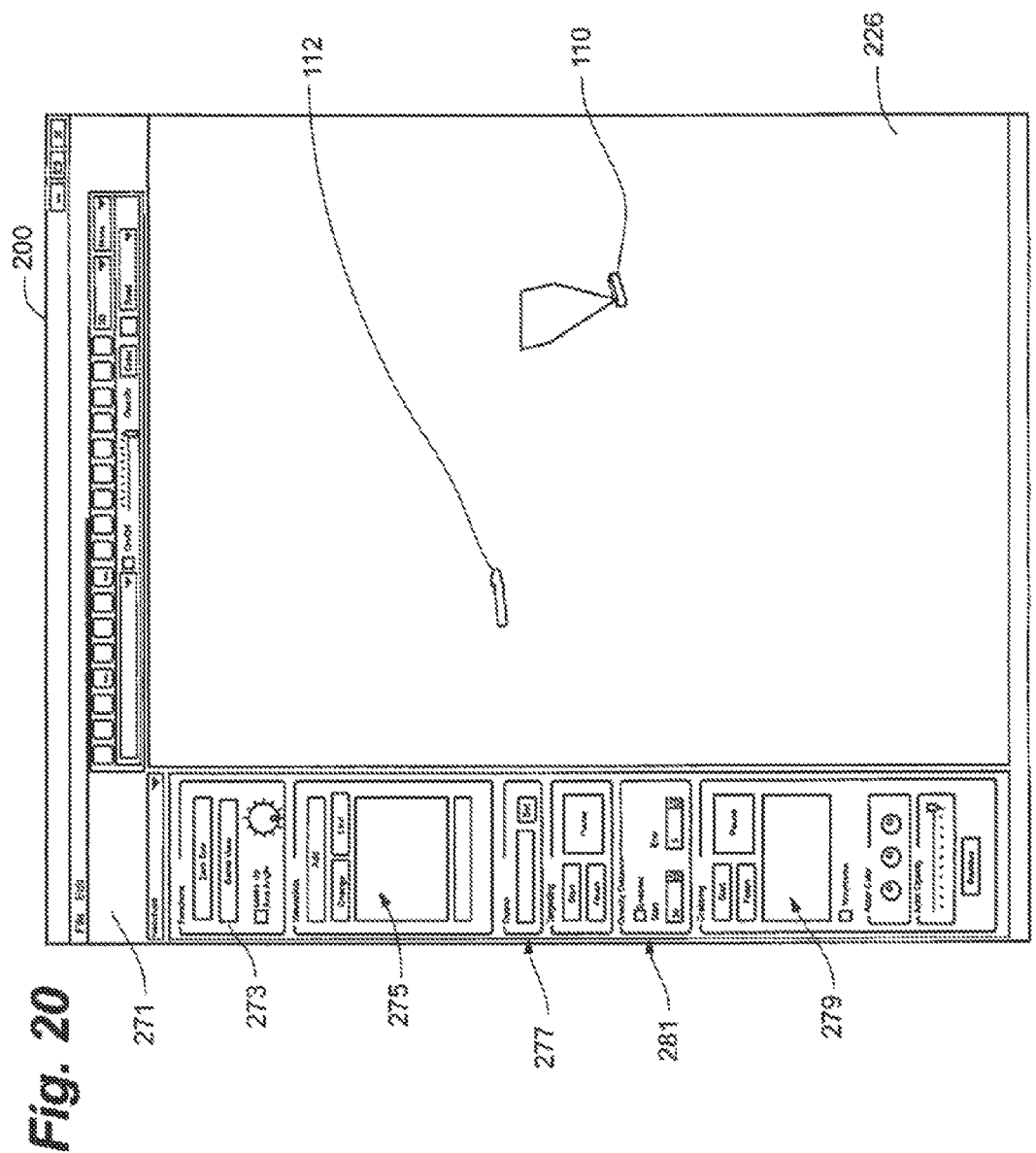

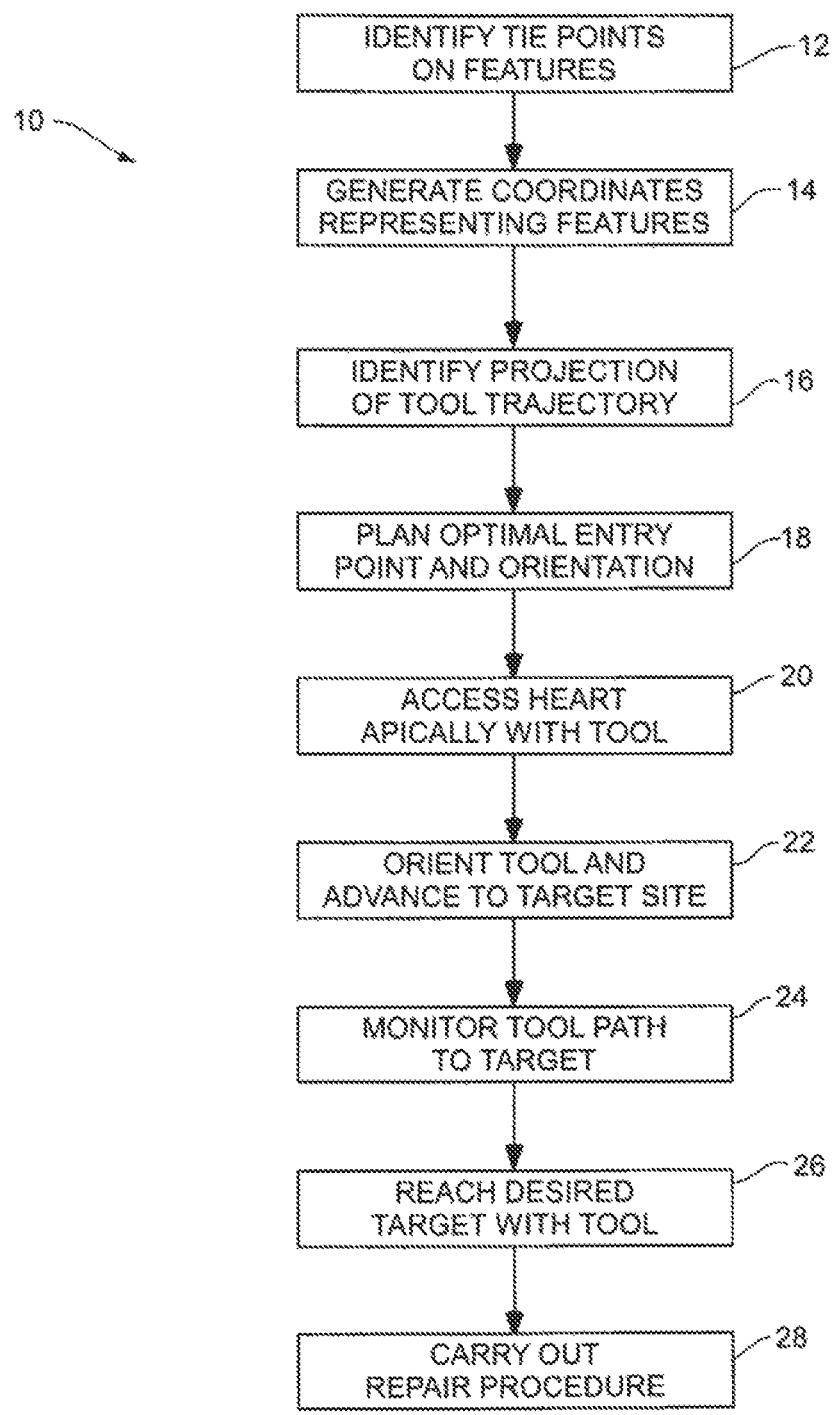

SURGICAL NAVIGATION FOR REPAIR OF HEART VALVE LEAFLETS

RELATED APPLICATION

This application is a continuation of U.S. patent application Ser. No. 13/692,027 filed Dec. 3, 2012, now U.S. Pat. No. 8,938,283, which claims the benefit of U.S. Provisional Application No. 61/565,795 filed Dec. 1, 2011, each of which is incorporated herein by reference.

FIELD OF THE INVENTION

The present invention relates to minimally invasive repair of heart valve leaflets. More particularly, the present invention relates to surgical navigation systems for minimally invasive repair of heart valve leaflets.

BACKGROUND OF THE INVENTION

Degenerative mitral valve disease (DMVD) is a common heart valve disorder in which there is incomplete valve closing, often resulting in shortness of breath, fluid retention, heart failure, and premature death. DMVD is characterized by abnormal connective tissue of the mitral valve, resulting in weakening and rupture of the chordae tendonae (chords), the support structures of the mitral valve, preventing its natural closure. DMVD affects about 2% of the general population and severe, symptomatic DMVD is treated by surgical repair or replacement. Major advances in mitral repair surgery have improved short- and long-term outcomes of patients with this disease. Many such procedures can also benefit individuals having functional mitral valve disease.

Open heart cardiac surgery is highly invasive with a long recovery period, and not well tolerated by elderly or co-morbid patients. Recent innovations in minimally invasive and robotic mitral repair techniques employ sternal sparing approaches to reduce the invasiveness of the procedure, but still require the use of cardiopulmonary bypass which has many associated complications. While the emerging field of transcatheter mitral valve repair avoids the risks of conventional surgery and potentially offers hopes of beating heart mitral valve reconstruction, concerns about residual mitral insufficiency, durability, and inadequate mitral valve repair have been raised.

Devices capable of performing off-pump, mitral valve repair for certain forms of DMVD, such as those disclosed in U.S. Patent Publication Nos. 2008/0188873, 2010/0174297, 2009/0105279 and 2009/0105751, have recently been developed. Such devices can use transapical access to approach and capture the prolapsed portion of the mitral valve leaflet, attach a suture and anchor it at the apex, constraining the flailing leaflet, and eliminating the prolapse. Currently, this procedure relies exclusively on trans-esophageal echocardiography (TEE) guidance in the form of 2D single plane, bi-plane, and 3D imaging. While TEE has thus far proven adequate for the final positioning of the tool and grasping the leaflet, there have been concerns relating to the navigation of the tool from the apex to the target MV leaflet. TEE guidance can be problematic as it may not always be possible to maintain appropriate spatial and temporal resolution in 3D, and it may not always be possible using single 2D and 2D bi-plane views to simultaneously maintain both the tool tip and target site in the field of view. Using 2D echo it also can be difficult to ensure that the tool tip, rather than a cross section of the tool shaft, is visualized. Due to these navigation challenges, the tool can become caught in the region below the valve leaflet, risking leaflet perforation.

After extensive animal studies, the devices described in the above-referenced publications are currently undergoing preliminary in-human trials for the repair of flailing mitral valves. The procedure uses off-pump trans-apical left ventricle (LV) access. Correct leaflet capture is verified using a fiber-optic based detection mechanism. After leaflet capture has been verified, an ePTFE (expanded polytetrafluoroethylene) suture is pulled through the leaflet and the tool is retracted with both ends of the suture. The suture is fixed at the leaflet with a girth hitch knot, adjusted under Doppler echo to ensure minimum mitral regurgitation (MR) and then secured at the apex using a pledget. Multiple neochordae are typically used to ensure optimal valvular function. The single largest problem in navigating the device to the MV target region is that echo imaging must simultaneously keep the target region (MV line of coaptation) and the tool tip in view.

As noted above, traditional approaches for repairing and replacing mitral valves have relied on placing the patient on cardiopulmonary bypass (on-pump) and accessing the arrested heart directly via a median sternotomy. However, because this approach has the potential for major undesired neurological, vascular, and immunological sequalae, there is a push towards performing such procedures in a minimally-invasive fashion. Preliminary experience on animals and humans has indicated that ultrasound guidance alone is often not sufficient for minimally invasive procedures. It would therefore be desirable for a system to provide enhanced surgical guidance in such minimally invasive procedures for repairing patient heart valves.

SUMMARY OF THE INVENTION

To improve the overall navigation process for minimally invasive repair of heart valve leaflets, an augmented reality technique capable of providing a robust three-dimensional context for transesophogeal echocardiography data has been developed. In the context of various embodiment of the invention, augmented reality essentially refers to a system in which the primary environment is virtual but the environment is augmented by ral elements. In this real-time environment, the surgeon can easily and intuitively identify the tool, surgical targets, and high risk areas, and view tool trajectories and orientations.

In one embodiment, a surgical navigation system is provided to aid in conducting a heart valve repair procedure. System can include a heart valve repair device and medical imaging system including an imaginrobe to provide real-time imaging of the anatomy of the patient. A tracking system can include one or more sensors incorporated into the heart valve repair device and imaging probe to track location and orientation data of those devices in real-time three-dimensional space. A computer processor can receive the imaging data from the imaging system and the location and orientation data from the tracking system and can also create virtual geometric models of the heart valve repair system and the imaging probe. At least one display device can present the virtual geometric models overlain onto the real-time imaging data in a common coordinate system showing the models moving in real-time based on the location and orientation data from the tracking system.

In a further embodiment, a surgical navigation system for use in aiding a surgical procedure can be provided. At least one sensor can be incorporated into an imaging probe of a medical imaging system and a heart valve repair device. Real-time imaging data can be acquired by the imaging system with the imaging probe. Virtual geometric models of the imaging probe and the heart valve repair device are also created. The virtual geometric models can then be overlain onto the imaging data in a common coordinate system. The location and orientation of the imaging probe and the heart valve repair device can subsequently be displayed in real-time three-dimensional space with tracking information obtained by the sensors.

The above summary of the various embodiments of the invention is not intended to describe each illustrated emboiment or every implementation of the invention. This summary represents a simplified overview of certain aspects of the invention to facilitate a basic understanding of the invention and is not intended to identify key or critical elements of the invention or delineate the scope of the invention.

BRIEF DESCRIPTION OF THE FIGURES

The embodiments of the present invention may be more completely understood in consideration of the following detailed description of various embodiments in connection with the accompanying drawings, in which:

FIG. 1 is a schematic representation of a surgical navigation system according to an embodiment of the present invention.

FIG. 2 is a perspective view of a surgical navigation system according to an embodiment of the present invention.

FIG. 3 is a partial view of a transesophageal echocardiogram probe that can be used with a surgical navigation system according to an embodiment of the present invention.

FIG. 4 is a perspective view of a heart valve repair system that can be used with a surgical navigation system according to an embodiment of the present invention.

FIG. 10 is a perspective view of a calibration system for a surgical navigation system according to an embodiment of the present invention.

FIG. 11 is a screenshot of a surgical navigation system according to an embodiment of the present invention.

FIG. 12 is a screenshot of a surgical navigation system according to an embodiment of the present invention.

FIG. 13 is a screenshot of a surgical navigation system according to an embodiment of the present invention.

FIG. 14 is a screenshot of a surgical navigation system according to an embodiment of the present invention.

FIG. 19 is a screenshot of a surgical navigation system according to an embodiment of the present invention.

FIG. 20 is a screenshot of a surgical navigation system according to an embodiment of the present invention.

FIG. 21 is a flowchart depicting steps of heart valve repair process according to an embodiment of the present invention.

Figure 5A:
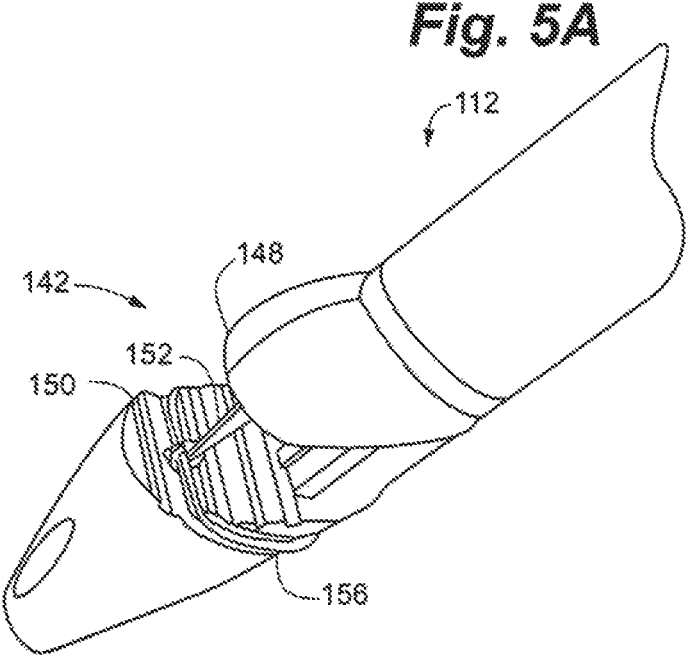
FIG. 5A is a partial perspective view of the heart valve repair system of FIG. 4.
Figure 5B:
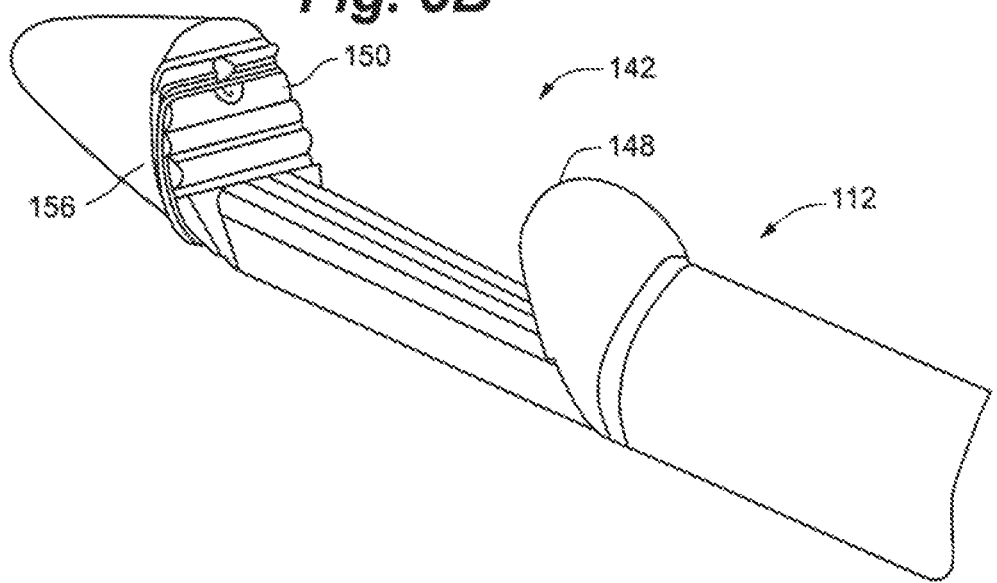
FIG. 5B is a partial perspective view of the heart valve repair system of FIG. 4.
Figure 6:
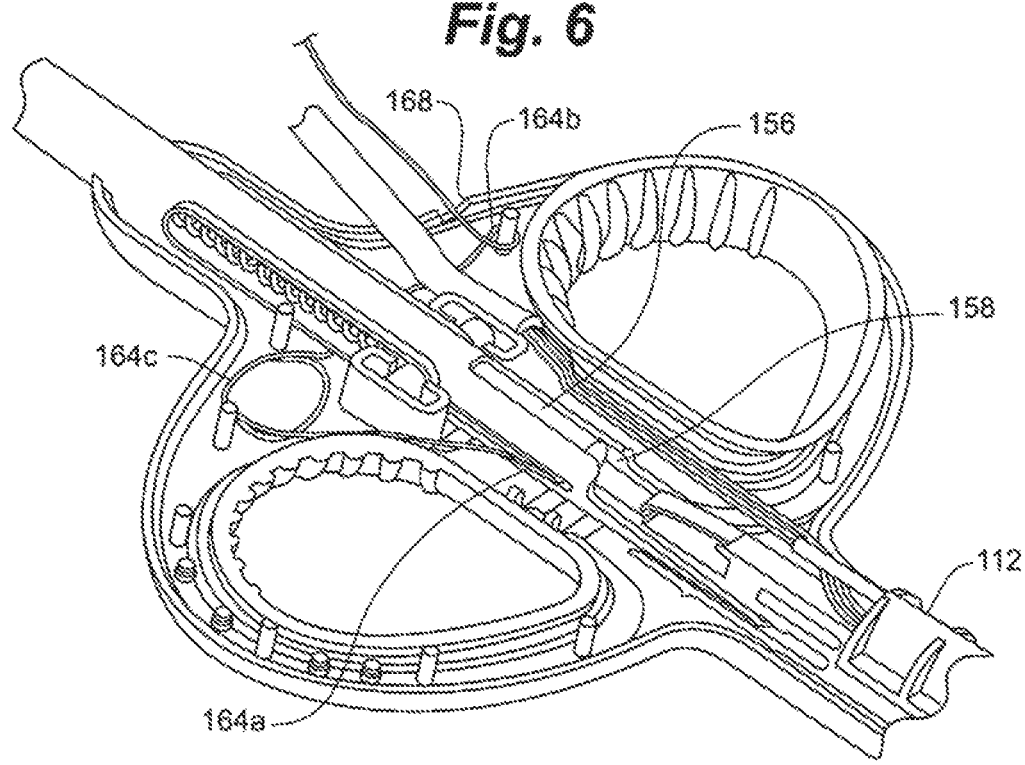
FIG. 6 is a partial perspective view of a heart valve repair system for use with a surgical navigation system according to an embodiment of the present invention.
Figure 7:
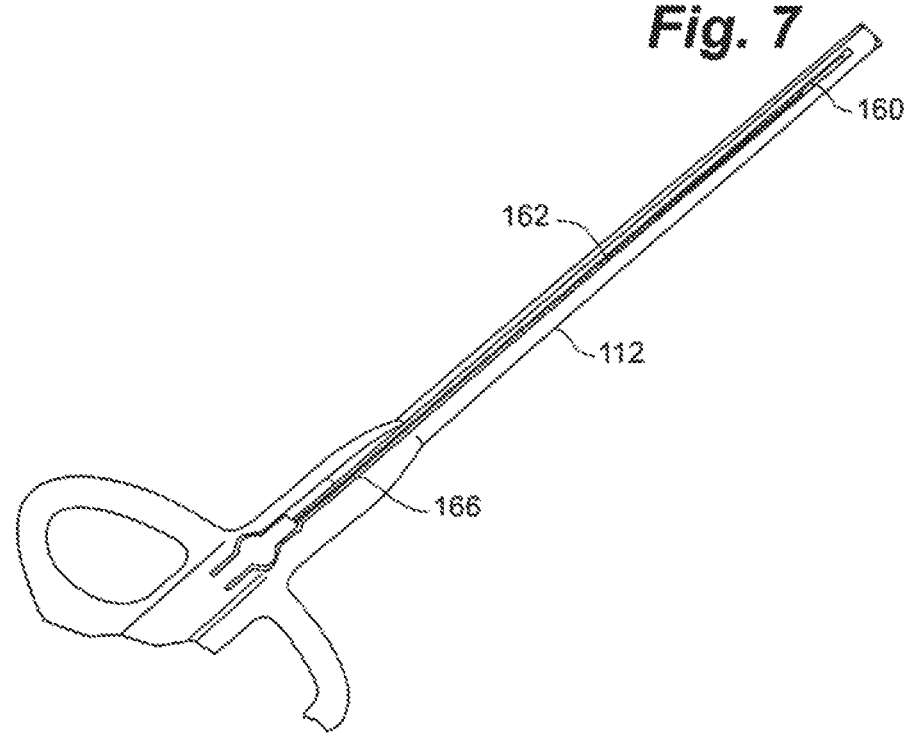
FIG. 7 is a partial perspective view of a heart valve repair system for use with a surgical navigation system according to an embodiment of the present invention.
Figure 8:
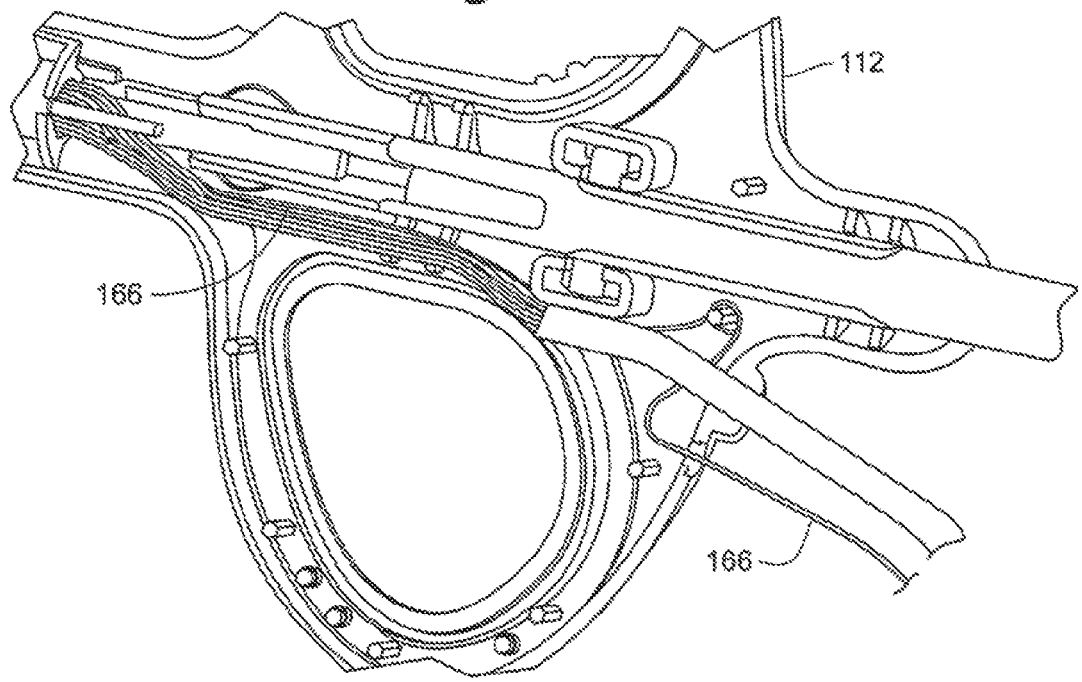
FIG. 8 is a partial perspective view of a heart valve repair system for use with a surgical navigation system according to an embodiment of the present invention.
Figure 9:
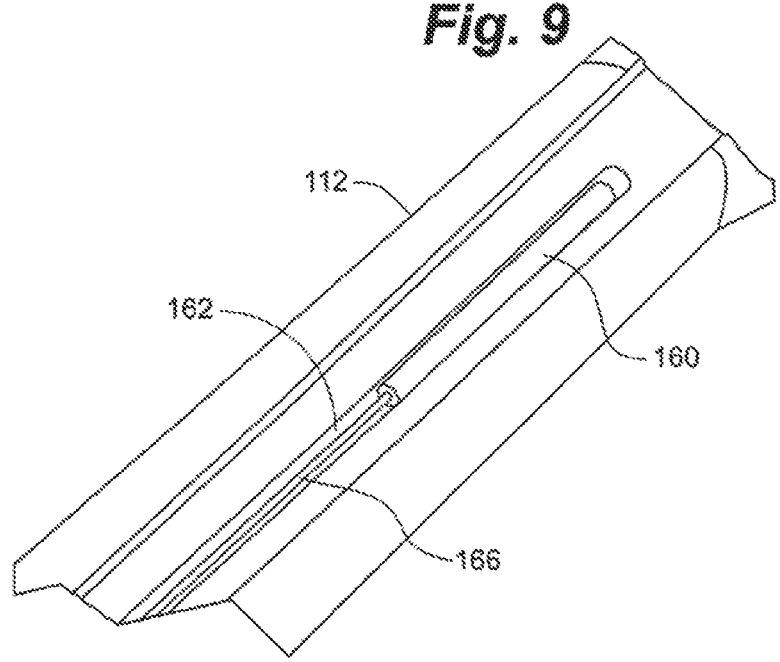
FIG. 9 is a partial perspective view of a heart valve repair system for use with a surgical navigation system according to an embodiment of the present invention.

While the present invention is amenable to various modifications and alternative forms, specifics thereof have been shown by way of example in the drawings and will be described in detail. It should be understood, however, that the intention is not to limit the present invention to the particur embodiments described. On the contrary, the invention is to cover all modifications, equivalents, and alternatives falling within the spirit and scope of the present invention.

DETAILED DESCRIPTION

In the following detailed description of the present invention, numerous specific details are set forth in order to provide a thorough understanding of the present invention. However, one skilled in the art will recognize that various embodiments of the present invention may be practiced without these specific details. In other instances, well-known methods, procedures, and components have not been described in detail so as to not unnecessarily obscure aspects of the present invention.

According to an embodiment of the present invention, a visualization environment uses tracking technology to locate both a heart valve repair tool and a transesophageal echocardiogram (TEE) probe in 3D space, making it possible to represent real-time echo images with virtual geometric models of both devices and interactively defined anatomy within a common coordinate system. Exemplary repair tools can include those disclosed in U.S. Patent Publication Nos. 2008/0188873, 2010/0174297, 2009/0105279 and 2009/0105751, each of which is incorporated by reference. Sensors from, for example, the Aurora (Northern Digital, Waterloo, Canada) magnetic tracking system (MTS) can be integrated into the repair tool and onto the TEE probe of a, for example, Philips iE33 ultrasound.

Geometric models of each device can be created with appropriate computer software and the tools appropriately calibrated. One embodiment of such geometric models can be implanted using the Visualization Toolkit (http://www.vtk.org/doc/release/5.0/html/classes.html) using spline filters and STL file readers found in the open-source VTK software libraries, which is incorporated by reference herein. Specifically, classes such as the vtkSTLREader and vtkSplineFilter can be utilized, each of which is incorporated by reference. Axes with 10mm markings can be projected from the virtual representation of the tool, indicating the forward trajectory of the tool and the direction of the opening jaws. The system greatly facilitates a surgeons' ability to plan the tool trajectory towards a desired target site, such as a heart valve.

In addition to representations of the tools, tracking the TEE image data makes it possible to define anatomy of interest (aortic valve annulus, target location (e.g., mitral valve line of coaptation), and regions to be avoided (e.g., mitral valve annulus) for contextual purposes. In the case of mitral valve repair, the objective is to identify the plane of the mitral valve annulus in order to be able to navigate the repair tool quickly and safely to the appropriate place within the valve annulus to proceed with the repair under. With regard to an aortic valve repair, a primary issue is identifying the critical structures associated with the valve so that a new valve can be placed in such a way that it does not block the coronary vessels fed by the coronary ostia and positioned appropriately with respect to the base of the aorta. In both types of procedures, target points can be identified with ultrasound shown as three dimensional locations in space that can be fitted with lines, rigs or planes to identify the location of the coronary ostia, annuli of the valves, the line or plane defining the base of the valve or any calcifications near the aortic valve. As will be described further herein, each of these marked regions can be updated to reflect its motion during the procedure, using motion models acquired from pre-operative images, by extracting motion parameters from the intra-operative ultrasound images, or by implanting and tracking one or more magnetically or sonically traced fiducial markers secured close to or on the respective target region.

This augmented reality system is designed to assist the surgeon with three related navigation tasks of; planning the access point and trajectory; maintaining a safe and direct entry through the mitral valve commisure into the left atrium, and establishing the correct tool orientation at the line of coaptation so the repair device can grasp the flailing leaflet. As shown in FIG. 21 such a process 10 includes, prior to making the apical entry incision, the echocardiographer identifying a minimal number of tie-points along the pertinent anatomy (aortic valve annulus, mitral valve annulus, line of coaptation) at step 12. From these coordinates, at step 14 a series of coordinates are generated to represent these features in virtual space. Next, the surgeon uses a desired trajectory projection of the repair tool determined at step 16 to plan the optimal entry point and orientation at step 18. After apical access at step 20, the surgeon simply orients and points the tool trajectory towards the desired target site and advances the tool at step 22, monitoring the virtual representations as seen on the real-time echo image data at step 24. By overlaying the virtual elements on the real echo image data, the surgeon is able to assess the accuracy and reliability of the virtual representations in real time. Once at the desired target location at step 26, the procedure can return to the standard workflow for carrying out the repair procedure at step 28, since additional guidance is no longer needed. In addition, any relevant structure that can be identified within or surrounding the heart in ultrasound, with a tracked electrophysiological device or which can be identified in preoperative image and registered into the ultrasound coordinate frame can be similarly incorporated into the system.

One embodiment of a surgical navigation system 100 as described above is depicted in FIGS. 1 and 2. The primary components of the system include a magnetic tracking system 102, an ultrasound imaging system 104 and a computer 106 with one or more output monitors 108. A TEE probe 110 of the ultrasound imaging system 104 can be integrated with the magnetic tracking system 102. A heart valve repair device 112 can also interface with the magnetic tracking system 102.

The magnetic tracking system 102 can utilize sensors interfacing with each of the TEE probe 110 and the heart valve repair device 112 to track the location and orientation of those tools with respect to the magnetic field generator 117 of the system 102, which can be placed on the operating room table underneath the patient. This information can be used to place both the TEE probe 110 and the heart valve repair device 112 into a common virtual environment. Each of the sensors can communicate with the magnetic sensor control unit 116 that is linked to each sensor by a sensor interface unit 118. In one embodiment, the system 102 uses the Northern Digital Aurora magnetic tracking system. In such an embodiment, the magnetic tracking system 102 is controlled using NDI API software 113 and interfaces with the navigation application suite 111 on the computer 106 with AIGS API software 114. The system can utilize three tracked sensors, one mounted to the TEE probe 110 and two mounted to the heart valve repair device. In other embodiments, greater or fewer sensors can be used with each device. Although described as using a magnetic tracking system 102 to track the ultrasound probe and surgical tools, it should be understood that various other tracking systems could be utilized in accordance with the present invention. For example, other types of tracking that could be used include acoustic, radio-frequency, fiber optic, image based and x-ray.

Referring now to FIG. 3, there can be seen a TEE probe 110 that can be used with embodiments of the present invention. The TEE probe 110 includes an ultrasound transducer that interacts with the ultrasound system 104 to provide echo images, as is known in the art. In the present invention, at least one sensor 130 is mounted to the TEE probe 110. Sensor 130 can be a six degree of freedom, magnetically tracked sensor. In one embodiment, as shown in FIG. 3, the sensor 130 is mounted on a side surface of the probe 110. In other embodiments, the sensor 130 can be mounted on an upper or lower surface of the probe or integrated inside the probe casing. Sensor 130 can be mounted to probe 110 with an adhesive, such as, for example a Loctite 3554 UV cured adhesive. Sensor 130 can be permanently or removably mounted to probe 110. In one embodiment, sensor 130 can be a single use, disposable sensor that can be utilized due to potential sensor damage and cleaning/sterilization issues that can arise with long term use. Sensor 130 can also be integrated into a removably mountable cap that can be mounted to the probe 110 during a procedure and then removed for cleaning prior to a subsequent procedure.

FIGS. 4-9 depict a heart valve repair device 112 that can be used with embodiments of the present invention. Device 112 generally includes a handle assembly 140 and a capture assembly 142 with an elongate shaft 144 extending therebetween. An actuator 146 is located at a proximal end of the device 112 for operating capture assembly 142. As can be seen in FIGS. 5A and 5B, capture assembly 142 can include a first clamping jaw 148 and a second clamping jaw 150. Clamping jaws 148, 150 are slidably disposably relative to each other with actuator and can be used to capture tissue, such as a heart valve leaflet, therebetween. Once tissue is captured between clamping jaws 148, 150 a needle 152 can penetrate the tissue to insert a suture 154 into the tissue. Further details of heart valve repair devices useable with the present invention are disclosed in U.S. Patent Publication No. 20090105751, which is incorporated by reference herein. Although one specific heart valve repair device is shown, it should be understood that the present invention can be adapted for use with any type of heart valve repair device.

Repair device 112 as used with the present invention can incorporate two sensors in addition to the sensor 130 utilized with the TEE probe 112. In one embodiment, a first sensor 156 can be disposed with a rubber cylinder positioned within a groove 158 in the shaft 144 of the device near the handle assembly 140. This sensor can be a five degree of freedom magnetic sensor that is used to track the opening and closing of the capture assembly 142 clamping jaws 148, 150. A second sensor 160 can also be disposed in a groove 162 in the shaft 144. The second sensor 160 can be a six degree of freedom magnetic sensor that is used to track the movement of the repair device 112 itself. In one embodiment, the second sensor 160 can be held in the groove by an adhesive. Each sensor 156, 160 includes corresponding wires 164, 166 through which the positional data is transmitted that are routed out of the tool 112 and back to the sensor interfaces 118 and sensor control unit 116. In one embodiment, the wires 164 for the first sensor are fixed to the shaft 144 at location 164a and again adjacent the exit point of wires 164 from device at location 164b, with a length of slack 164c that allows the sensor to move along the shaft 144 when actuator 146 is employed to move the clamping jaws 148, 150. Wires 166 for second sensor 160 can be adhered to the shaft 144 until the wires 166 exit the device 112. Wires 164, 166 can exit through an opening 168 in the body of the repair tool 112. In one embodiment, opening includes a grommet through which the wires 164, 166 extend.

One or both of the heart valve repair device 112 and the TEE probe 110 can be calibrated for use with the system 100. In this context, calibration refers to the process of defining the coordinate frame of a device relative to the magnetic tracking sensors or other sensors used to track the device. Heart valve repair device 112 can be calibrated with a calibration jig 170 such as shown in FIG. 10. The jig 170 is configured such that the tip of the repair device 112 is always in the same location when held in the jig 170. In one embodiment, the jig 170 can comprise two milled acrylic blocks. A reference sensor 172 is positioned near the tip of the repair device 112 and can be rigidly mounted to the jig 170. In one embodiment, the sensor can be an NDI Aurora sensor. The jig 170 can also include a series of divots 174 milled into the jig 170 near the tip of the repair device 112. In one embodiment, eight spherical divots are milled in a non-symmetrical pattern. A geometric model of the jig 170 can be created from a micro-CT of the jig, with the origin of the model defined at the repair device 112 tip and the z-axis extending along the long axis of the repair device 112. Using the micro-CT data, the locations of the milled divots are then defined for the model. Then, a magnetically tracked tool 176 is used to calibrate the repair device 112 by interfacing the tool 176 with each of the divots 174. In one embodiment, a tip 178 of the tool 176 can be shaped to fit within the divots 174. In one embodiment, the device 112 can be provided to an end user having been pre-calibrated for use during production.

The TEE probe 110 can be calibrated by using a magnetically tracked tool intersecting the ultrasound image plane. In one embodiment, the magnetically tracked tool can be a previously calibrated repair device 112. In one embodiment, the computer 106 can monitor the accuracy of the calibration during a surgical procedure and warn the users of potential inaccuracies in the model. In such an embodiment, the system could also intra-operatively correct calibration errors during the procedure.

The ultrasound image data acquired by the TEE probe 110 is transmitted from the ultrasound system 104 to the computer 106 for integration into the virtual scene created with the system 100. The data can be transferred from the ultrasound system 104 to the computer with a converter 120. In one embodiment, the converter is the Epiphan DVI2USB converter. In such an embodiment, the converter 120 can be managed by the Epiphan Application Program Interface 121.

The computer 106 operates to integrate image data from the ultrasound system 104 with tracking information from the magnetic tracking system 102 to present virtual representations of the heart valve repair tool 112 and TEE probe 110 in a common 3D environment. Using the tracked TEE image data, geometric models of pertinent anatomy, such as mitral and aortic valve annuli, are added to provide the surgeon with a significantly more intuitive environment for performing the surgical procedure, as will be described in more detail below.

In one embodiment, two monitors 108 are used to provide a split screen view of the system. In such an embodiment, one monitor can be used for viewing by the surgeon and the other can be used by the echocardiographer and technician. In other embodiments, only one monitor can be used or more than two monitors can be used.

The computer 106 can operate a software platform that provides an augmented reality viewpoint for a surgeon performing a procedure, such as repair of a heart valve. The software platform provides the system for integrating the real-time information from the magnetic tracking system 102 with the real-time information from the ultrasound system 104, 110. The information is displayed on a user interface 200 on the one or more computer monitors 108 showing the ultrasound image data with dynamic virtual geometric representations of surgical tools 202 and anatomy 204 as will be discussed in more detail with regard to FIGS. 11-20.

To establish the user interface, the software platform must render the various components for display on the interface. The body or shaft 144 of the heart valve repair device 112 can be rendered on the system as a solid shape derived from CAD drawings of the device. Either a portion of the length of the body of the device (e.g., 2 cm or 4 cm) or the full body can be rendered. The tip or capture assembly 142 can also be generated from CAD drawings using the same calibration matrix as the body. The location where the needle 152 used by the device to penetrate tissue exits from the shaft 144 can be marked with a sphere 206. The sphere can define two axes, a first axis 208 can be aligned with the direction of the tool trajectory, and a second axis 210 can be orthogonal to the first axis 208. Repair device 112 can be displayed either as opaque or transparent object. In one embodiment, the device 112 automatically fades to transparency as it approaches target tissue, with distances at which this occurs selectable by the user. In such an embodiment, the sphere marker 206 showing the location of the needle can remain opaque at all times.

FIG. 13 depicts an opening screen 220 of the user interface 200 according to an embodiment of the present invention. Opening screen 220 can include a general functions render pane 222 that allows rendering of an object to be manipulated and a module render pane 224 for displaying specific operations that can be undertaken in a given module. The scene render pane 226 will display the navigation data for a given procedure. A drop down menu 228 can be used to access the user interfaces for various modules.

A tracked tool module 230 is displayed in FIG. 14. A tracked tools dialog window 232 shown in FIGS. 15-18 can be opened by selecting the corresponding button 233 on the tracked tool module 230. A tracker pull down menu 234 can be used to select a specific tracked tool. Once a tool is selected, tracker control buttons 236 can be used to control tracking of the tool. The opacity of all tools can be controlled with the global tool opacity slider 238. Opacity of a specific tool can also be adjusted on the tracked tool module 230 by selecting from the tool pull down bar 240 and using the corresponding slider 242. Display of the selected tool in wireframe and display of the tool axes can also be turned off and on with corresponding check boxes 244, 246 on the tracked tool module 230.

Figure 15:
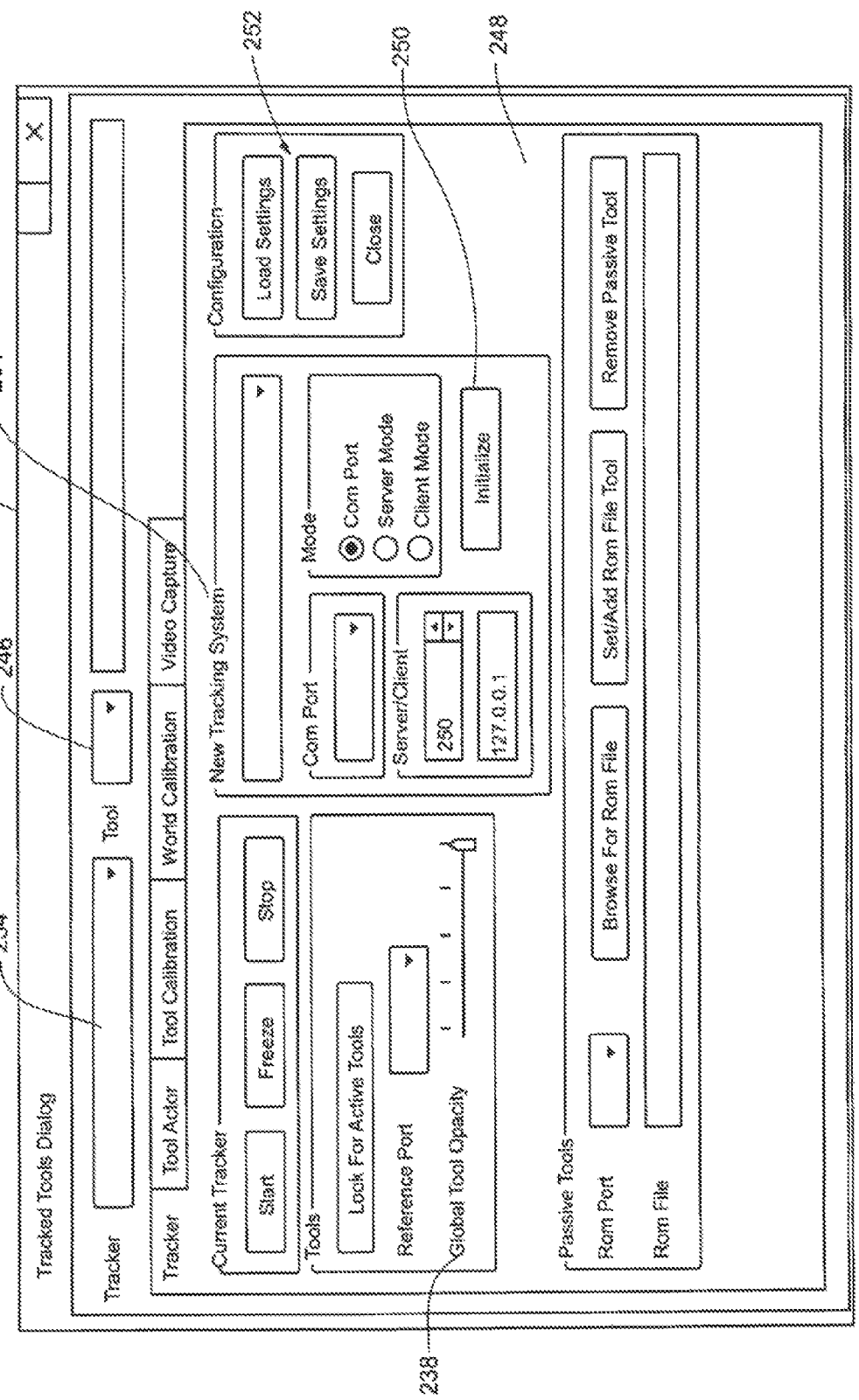
FIG. 15 is a screenshot of a surgical navigation system according to an embodiment of the present invention.

FIGS. 15-18 display various aspects of the tracked tools dialog window 232, which can provide the basic functionality of the tracked tool module 230 as well as additional functionality. A tracker pane 248 of the window 232 is shown in FIG. 15, and includes a tracker pull down menu 234 and tracker control buttons 235. A tool pull down menu 240 allows selection of a specific tool. A new tracking system box 251 allows a new system to be added with an initialize tracker button 250 to actuate the new system. A specific configuration for a tracking can be loaded or saved with buttons in the configuration box 252.

Figure 16:
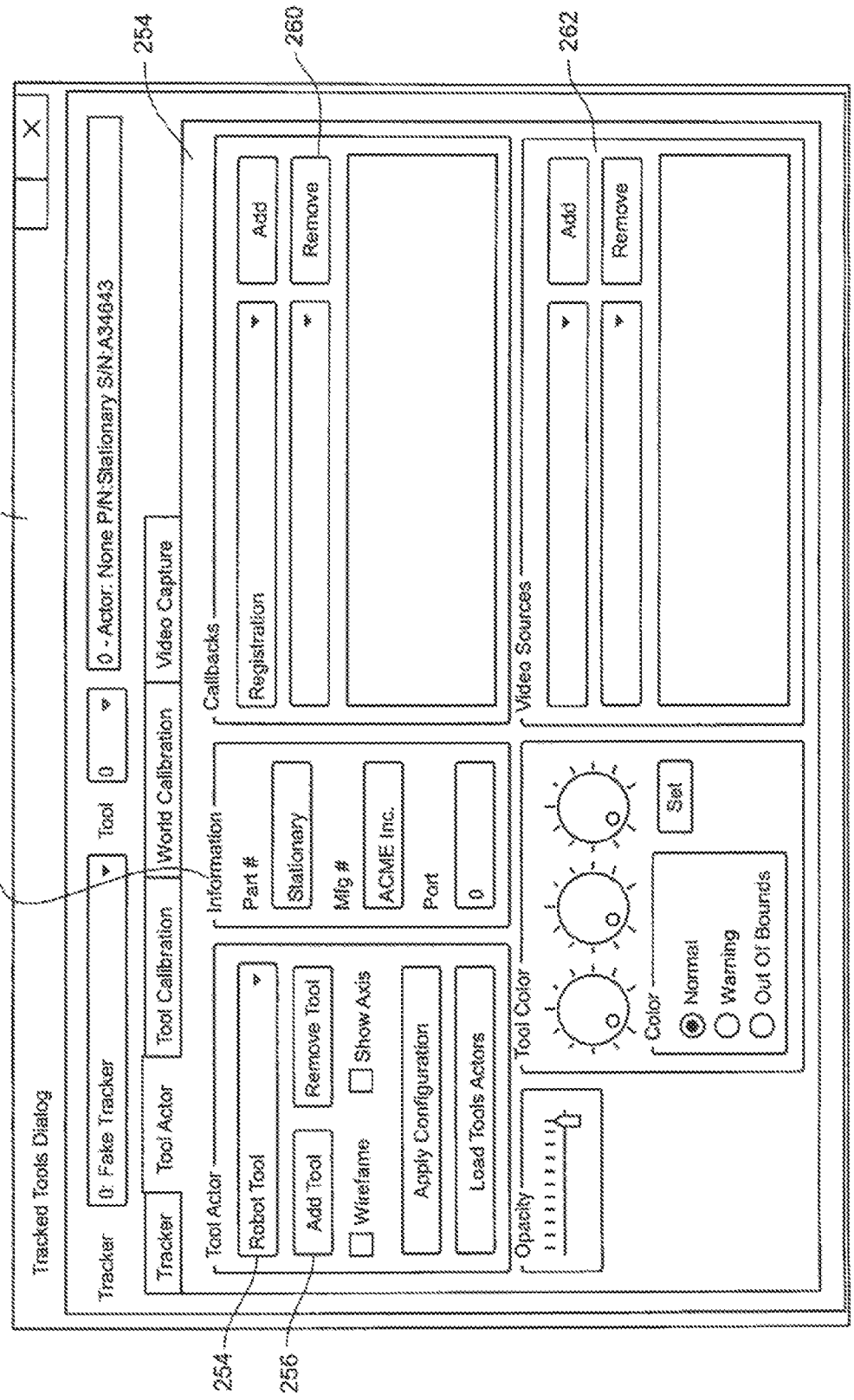
FIG. 16 is a screenshot of a surgical navigation system according to an embodiment of the present invention.

A tool actor pane 252 of the tracked tools dialog window 232 is shown in FIG. 16. The tool actor pane 252 allows all virtual actors to be interactively modified in real time. The tool actor can be selected from a tool actor dropdown 254 and a new tool can be rendered with the add tool button 256 after an acting tool is selected. Various information on the tool can be provided and modified in the information box 258. Callbacks for the tool are contained in a callbacks box 260. Video sources for use with the tracked tool can be added, removed, and viewed in the video sources box 262.

Figure 17:
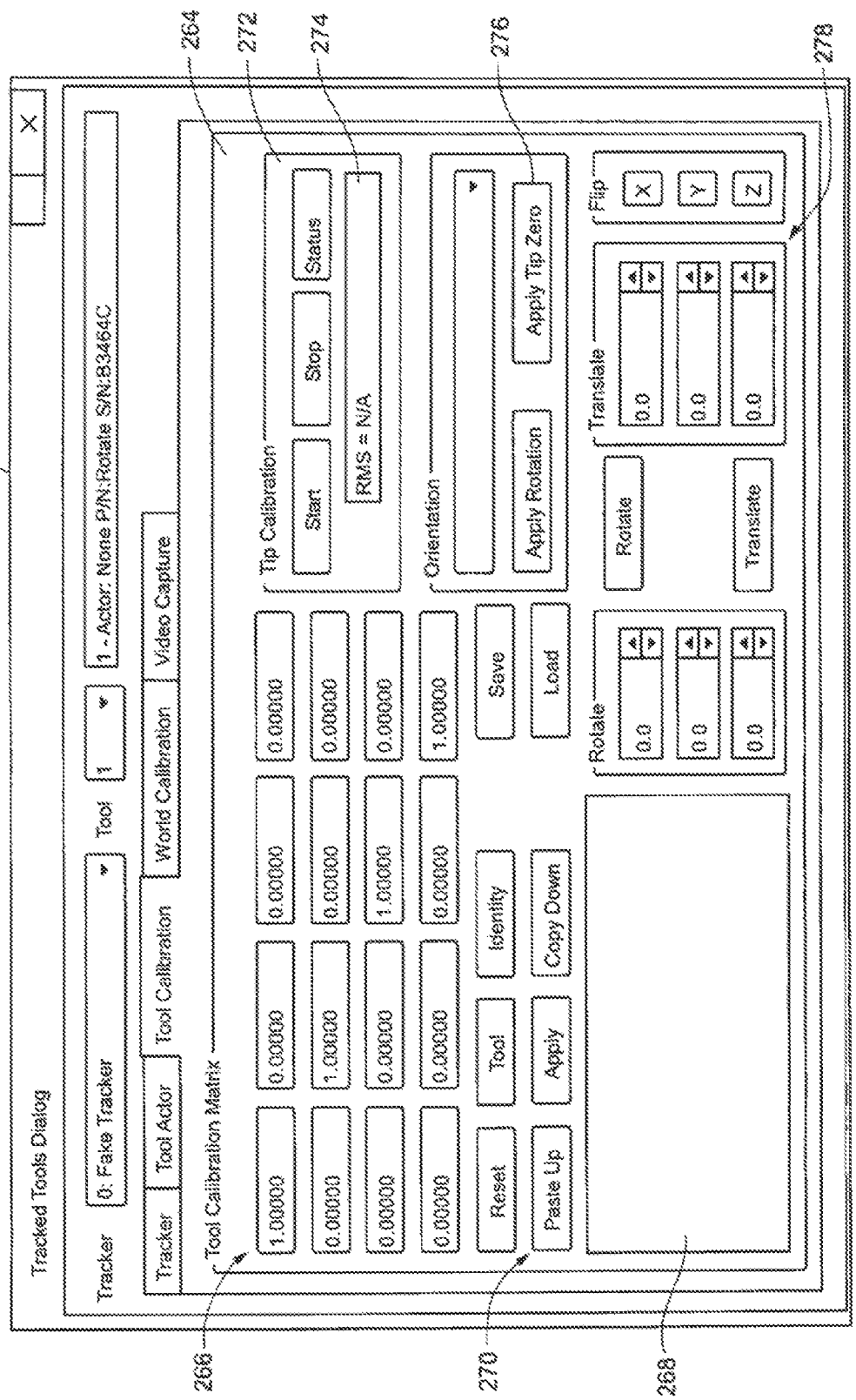
FIG. 17 is a screenshot of a surgical navigation system according to an embodiment of the present invention.
Figure 18:
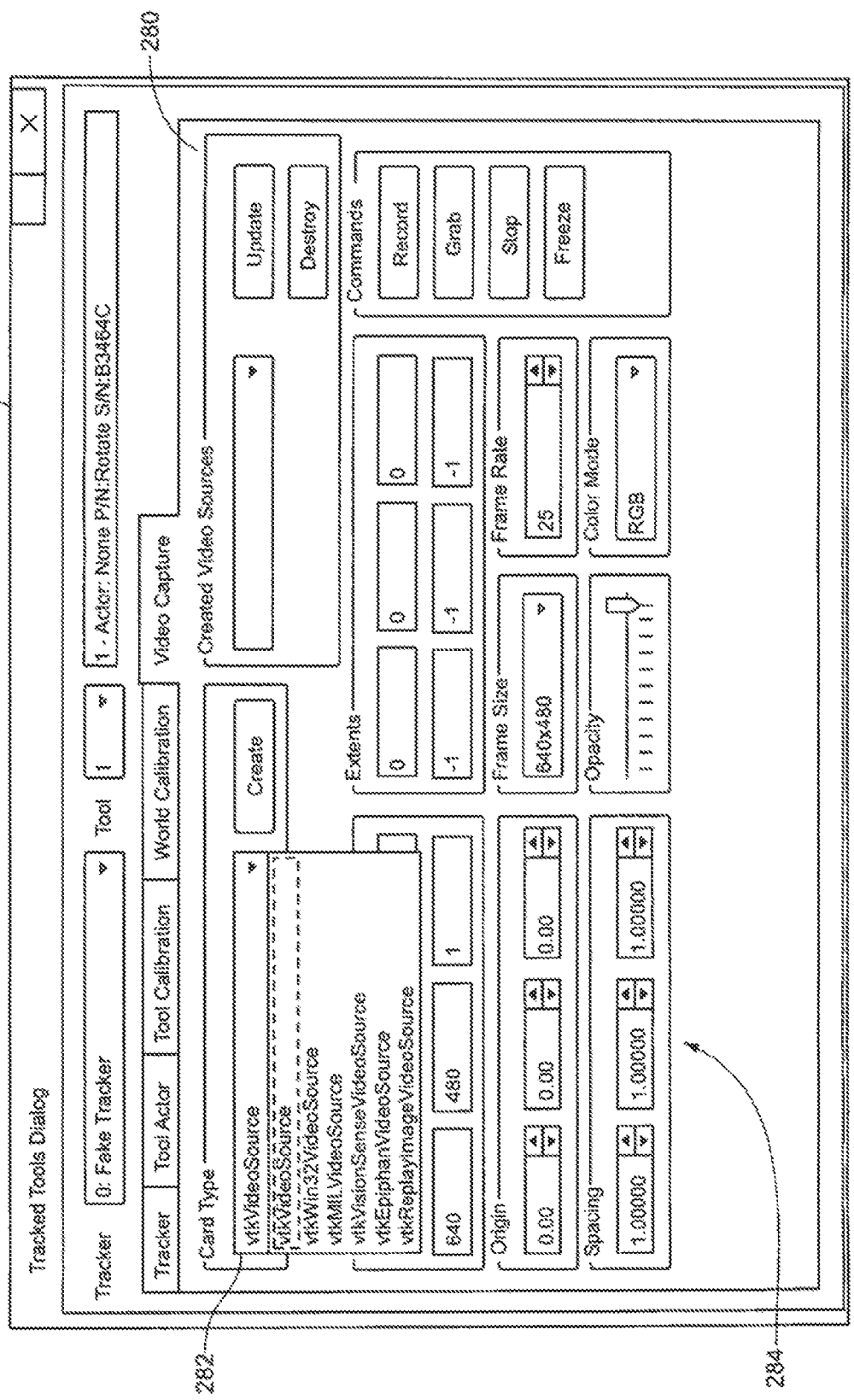
FIG. 18 is a screenshot of a surgical navigation system according to an embodiment of the present invention.

The tool calibration matrix 266 is displayed on a tool calibration pane 264 of the dialog box 232 as shown in FIG. 17. The matrix can be manually entered into the boxes or can be copied and pasted into a text box 268. Various matrix controls 270 for manipulating the data are also provided. A tip calibration box 272 can allow calibration of a tool tip and can also display the root mean squared error of the calibration 274. The orientation and tip location of a tool can also be obtained from a previously saved tool with the orientation box 276. A command box 278 can alternatively be used to manually calibrate the rotation and translation controls. The tracked tools dialog window 232 can also include a video capture pane 280 as shown in FIG. 18. This pane can provide for selection of a specific source video card from a pull down menu 282 and display information 284 about the source.

An anatomical feature module 286 is shown in FIG. 19. A drop down menu 288 and associated controls allow a specific anatomical feature to be selected, added, or removed, such as for example, the mitral valve or the aortic valve. Various controls 290 can be used to adjust the rendering of the anatomical feature 289. A plurality of function keys 292 is also provided. Keys 292 can be used to manage tie points 294, which can be denoted by small spheres on the interface 200. Tie points 294 can be one or more 3-dimensional points representing a tracked location on an anatomical landmark such as the annulus of the mitral valve or aortic valve or other structure as described earlier. The tie points can be used to create a model of the structure with a suitable curve. Tie points can also be displayed to represent specific points on the structure, such as a desired grasping point along a valve leaflet. The save/load data buttons 296 allow tie points to be saved into the system or loaded from memory. A manage data menu 298 allows the tie point data to be edited and removed. In an alternative embodiment, tie points can be selected and defined on the ultrasound device 104, rather than on the computer 106.

In one embodiment, anatomical structures can be tracked as they move, either by using image-based tracking or by introducing tracked sensors close or attached to the anatomical structures. The tracking information can be used to dynamically update the virtual representations of the anatomy created with the tie points. An advantage of updating the target regions dynamically during the procedure is that in the case of mitral valve repair, the repairing instrument is less likely to be inadvertently guided into an inappropriate structure, causing potential damage. In the case of the aortic valve, the advantage of dynamically moving the target structures is that the procedure can be carried out without temporarily stopping the heart or inducing rapid pacing, both of which would stop the target motion, but would add additional risk to the patient.

A repair device module 271 is shown in FIG. 20. The scene render pane 226 displays the tracked repair tool 112 and TEE probe 110. Functions buttons 273 can be used to control various aspects of the devices. Various viewpoints from which the user can view the procedure can be selected and modified with viewpoints controls 275. The scene render pane 226 can display viewpoints in various ways, including a single view, a split, two pane view, and a four pane view. The viewpoint of the virtual camera for a specific view can be controlled with the computer mouse, which can rotate, pan, zoom, etc. the view, to allow the user to define a specific view. One view that can be utilized is a barrel view, which sets the camera a set distance, such as 10 cm, above the repair tool 112 aligned along the main axis of the tool 112. Barrel view can be activated with a corresponding function button 273. In an alternative embodiment, rather than the user defining and controlling the viewing angles for the augmented virtual reality scene, the viewing angles can be automated for a specific type of procedure. Views can also be based on pre-operatively acquired data. In an alternative embodiment, the images can be displayed stereoscopically to the observer. Navigation output controls 277 provide tracking and control of data relating to navigation of the repair device 112 to the target tissue structure and grasping controls 279 provide tracking and control of data relating the grasping function of the repair tool 112 clamping jaws 148, 150. These tracking functions can be activated manually, or can be performed automatically and can provide for recording, storage, and later playback. Automatic opacity of the tool at specific distances from the target site can be controlled with opacity controls 281.

It has been found that a surgical navigation system such as system 100 can significantly reduce the surgical time needed to perform a minimally invasive procedure, such as repair of a heart valve leaflet. In one study, the mean task completion time fell by a factor of almost six when using such a system. Such a system also leads to more direct navigation paths to the target tissue, which results in a safer procedure. For example, in repair of a heart valve leaflet, a repair device can inadvertently enter an area dangerous to a patient, such as the left ventricular outflow tract or cause damage to the leaflet itself when the path to the tool is not guided as described herein.

Although described herein as providing surgical navigation for capturing heart valve leaflets, embodiments of the present invention can also be applied to targeting any intracardiac structure for repair or replacement, such as full valve replacement or other structural heart repair. Sutures and other repair devices can be delivered via the disclosed system for repair purposes.

In a further embodiment, a surgical navigation system as described herein can be utilized as a training system. Thus, in lieu of utilizing the system to aid in guiding an actual surgical procedure, the system can be utilized to train surgeons, echocardiographers, and others for performing heart repair procedures.

Various embodiments of systems, devices and methods have been described herein. These embodiments are given only by way of example and are not intended to limit the scope of the present invention. It should be appreciated, moreover, that the various features of the embodiments that have been described may be combined in various ways to produce numerous additional embodiments. Moreover, while various materials, dimensions, shapes, implantation locations, etc. have been described for use with disclosed embodiments, others besides those disclosed may be utilized without exceeding the scope of the invention.

The invention claimed is:

1. A surgical navigation system configured to be used with a heart valve repair device, a tracking system including a device sensor configured to be integrated with the heart valve repair device to track location and orientation data of the heart valve repair device in real-time three dimensional space, and a medical imaging system including an imaging probe that is movable relative to a patient to provide real-time imaging data of anatomy of the patient, the surgical navigation system comprising:

a probe sensor configured to be integrated with the imaging probe, the probe sensor enabling the tracking system to track location and orientation data of the imaging probe in real-time three-dimensional space;

software operable on a computing device, the software configured to cause the computing device to:

receive the real-time imaging data from the medical imaging system;

receive the location and orientation data of the heart valve repair device and imaging probe from the tracking system;

create virtual geometric models of the heart valve repair device and the imaging probe; and cause the virtual geometric models of the heart valve repair device and the imaging probe to be overlain onto the real-time imaging data in a common coordinate system on a display device such that the virtual geometric models move in real-time according to the location and orientation data of the heart valve repair device and the imaging probe.

2. The surgical navigation system of claim 1, wherein the software is further configured to cause the computing device to create virtual geometric models of one or more anatomical features of the patient based on the real-time imaging data and cause the display device to present the virtual geometric models of the one or more anatomical features along with the virtual geometric models of the imaging probe and heart valve repair device in the common coordinate system.

3. The surgical navigation system of claim 2, wherein the software is further configured to automatically dynamically update a location and orientation of one or more of the virtual geometric models of the one or more anatomical features based on movement of the corresponding anatomical features.

4. The surgical navigation system of claim 1, wherein the sensors are configured to be magnetically tracked by the tracking system.

5. The surgical navigation system of claim 1, further comprising an actuation sensor, the actuation sensor configured to be incorporated into the heart valve repair device along with the device sensor.

6. The surgical navigation system of claim 5, wherein the device sensor is configured to track a body portion of the heart valve repair device and the actuation sensor is configured to track an actuation portion of the heart valve repair device.

7. The surgical navigation system of claim 1, further comprising a calibration jig and a calibration tool configured to be tracked by the tracking system, the calibration jig configured to hold the heart valve repair device as the calibration tool is used to define a coordinate frame of reference of the heart valve repair device relative to the device sensor.

8. A method for use with a heart valve repair device, a tracking system including a device sensor configured to be integrated with the heart valve repair device to track location and orientation data of the heart valve repair device in real-time three dimensional space, and a medical imaging system including an imaging probe that is movable relative to a patient to provide real-time imaging data of anatomy of the patient, the method comprising:

providing a probe sensor configured to be integrated with the imaging probe that is movable relative to the patient to enable the medical imaging system to provide the real-time imaging data of anatomy of the patient, the probe sensor enabling the tracking system to track location and orientation data of the imaging probe in real-time three-dimensional space;

providing software operable on a computing device, the software configured to cause the computing device to:

receive the real-time imaging data from the medical imaging system;

receive the location and orientation data of the heart valve repair device and imaging probe from the tracking system;

create virtual geometric models of the heart valve repair device and the imaging probe; and cause the virtual geometric models of the heart valve repair device and the imaging probe to be overlain onto the real-time imaging data in a common coordinate system on a display device such that the virtual geometric models move in real-time according to the location and orientation data of the heart valve repair device and the imaging probe.

9. The method of claim 8, wherein the software is further configured to cause the computing device to create virtual geometric models of one or more anatomical features of the patient based on the real-time imaging data and cause the display device to present the virtual geometric models of the one or more anatomical features along with the virtual geometric models of the imaging probe and heart valve repair device in the common coordinate system.

10. The method of claim 9, wherein the software is further configured to automatically dynamically update a location and orientation of one or more of the virtual geometric models of the one or more anatomical features based on movement of the corresponding anatomical features.

11. The method of claim 8, wherein the sensors are configured to be magnetically tracked by the tracking system.

12. The method of claim 8, wherein the tracking system further includes an actuation sensor, the actuation sensor configured to be incorporated into the heart valve repair device along with the device sensor.

13. The method of claim 12, wherein the device sensor is configured to track a body portion of the heart valve repair device and the actuation sensor is configured to track an actuation portion of the heart valve repair device.

14. The method of claim 8, further comprising providing a calibration jig and a calibration tool configured to be tracked by the tracking system, the calibration jig configured to hold the heart valve repair device as the calibration tool is used to define a coordinate frame of reference of the heart valve repair device relative to the device sensor.

15. A surgical navigation system configured to be used with a heart valve repair device, a medical imaging system including an imaging probe that is movable relative to a patient to provide real-time imaging data of anatomy of the patient, and a tracking system including a device sensor configured to be integrated with the heart valve repair device to track location and orientation data of the heart valve repair device in real-time three dimensional space and a probe sensor configured to be integrated with the imaging probe to track location and orientation data of the imaging probe in real-time three-dimensional space, the surgical navigation system comprising:

software operable on a computing device, the software configured to cause the computing device to:

receive the real-time imaging data from the medical imaging system;

receive the location and orientation data of the heart valve repair device and imaging probe from the tracking system;

create virtual geometric models of the heart valve repair device and the imaging probe; and cause the virtual geometric models of the heart valve repair device and the imaging probe to be overlain onto the real-time imaging data in a common coordinate system on a display device such that the virtual geometric models move in real-time according to the location and orientation data of the heart valve repair device and the imaging probe.

16. The surgical navigation system of claim 15, wherein the software is further configured to cause the computing device to create virtual geometric models of one or more anatomical features of the patient based on the real-time imaging data and cause the display device to present the virtual geometric models of the one or more anatomical features along with the virtual geometric models of the imaging probe and heart valve repair device in the common coordinate system.

17. The surgical navigation system of claim 16, wherein the software is further configured to automatically dynamically update a location and orientation of one or more of the virtual geometric models of the one or more anatomical features based on movement of the corresponding anatomical features.

18. The surgical navigation system of claim 15, wherein the sensors are configured to be magnetically tracked by the tracking system.

19. The surgical navigation system of claim 15, further comprising an actuation sensor, the actuation sensor configured to be incorporated into the heart valve repair device along with the device sensor.

20. The surgical navigation system of claim 19, wherein the device sensor is configured to track a body portion of the heart valve repair device and the actuation sensor is configured to track an actuation portion of the heart valve repair device.

21. The surgical navigation system of claim 15, further comprising a calibration jig and a calibration tool configured to be tracked by the tracking system, the calibration jig configured to hold the heart valve repair device as the calibration tool is used to define a coordinate frame of reference of the heart valve repair device relative to the device sensor.

* * * * *